United States Patent

Leenders

[11] 4,214,102
[45] Jul. 22, 1980

[54] AMINO-ETHER AMPHOTERIC SURFACE-ACTIVE COMPOUNDS

[75] Inventor: Peter Leenders, Allendale, N.J.

[73] Assignee: Henkel Inc., Hoboken, N.J.

[21] Appl. No.: 896,294

[22] Filed: Apr. 14, 1978

[51] Int. Cl.$^2$ .............. C07C 143/14; C07C 101/30; C11D 1/18; C11D 3/30
[52] U.S. Cl. .............. 562/564; 260/513 N; 252/545; 252/546
[58] Field of Search .............. 562/564; 260/513 N

[56] References Cited

U.S. PATENT DOCUMENTS

| | | | |
|---|---|---|---|
| 2,781,379 | 2/1957 | Mannheimer | 562/564 |
| 2,927,901 | 3/1960 | Charret | 562/564 |
| 3,210,410 | 10/1965 | Gaertner | 260/513 N |
| 3,778,268 | 12/1973 | Ushiyama | 260/513 N |
| 3,855,156 | 12/1974 | Marumo | 562/564 |
| 4,001,285 | 1/1977 | Hochreuter | 260/513 N |
| 4,039,565 | 8/1977 | Throckmorton | 562/564 |
| 4,044,034 | 8/1977 | Christiansen | 562/564 |
| 4,076,743 | 2/1978 | Koch | 562/564 |

Primary Examiner—Norman Morgenstern
Assistant Examiner—Michael Shippen
Attorney, Agent, or Firm—Hammond & Littell, Weissenberger and Muserlian

[57] ABSTRACT

An amino-ether amphoteric surface-active compound mixture produced by reacting a glycidyl ether having the formula

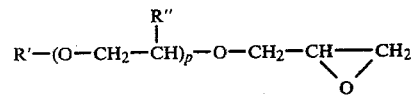

wherein R" is a member selected from the group consisting of hydrogen and methyl; R' is a member selected from the group consisting of aliphatic primary alkyl having from 8 to 22 carbon atoms, aliphatic primary alkenyl having from 12 to 20 carbon atoms and 2-alkylalkanols having from 10 to 36 carbon atoms; and p is an integer from 0 to 3; with a substantial excess of an N-hydroxy-$C_{2-4}$-alkyl-$C_{2-6}$-alkylene diamine, removing the excess diamine, reacting the resulting substituted amino-ether with an excess of an N-alkylating agent selected from the group consisting of halo-$C_{2-4}$-alkanoic acids, halo-$C_{2-4}$-alkane sulfonic acids and halo-$C_{3-4}$-hydroxyalkane sulfonic acids, under alkaline reaction conditions and recovering said amino-ether amphoteric surface-active compound mixture.

4 Claims, No Drawings

AMINO-ETHER AMPHOTERIC SURFACE-ACTIVE COMPOUNDS

BACKGROUND OF THE INVENTION

Amphoteric surface-active compounds of many different types have been utilized in washing agent compositions. They are of particular interest for use in hair shampoo formulations due to their low irritation to the eyes. It has been found that the products based on diamines have the least effect on the conjunctiva.

Products based on diamines, however, are often described as having an imidazoline ring, as for example, U.S. Pat. No. 3,849,315. In this patent imidazoline surfactants are disclosed having the formulae

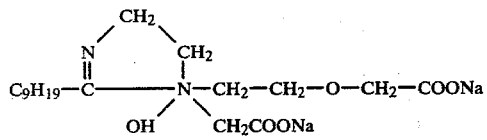

However, such imidazoline structures are actually difficult to obtain since, in the presence of water, they readily hydrolyze to give a linear structure

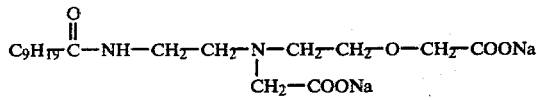

Such products are sold under the trademark Miranol ®. Such products, however, gradually break down in both alkaline and acidic solutions forming, over a period of time, turbidity in their solutions.

In addition, other types of compounds based on diamines, which have surface-active properties, have been disclosed. For example, U.S. Pat. No. 2,927,901 discloses compounds of the formula

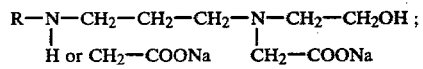

U.S. Pat. No. 2,993,918 discloses compounds of the formula

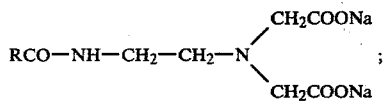

U.S. Pat. No. 3,813,422 discloses compounds of the formula

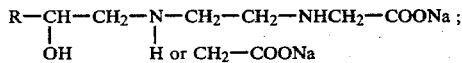

and U.S. Pat. No. 3,888,797 discloses compounds of the formula

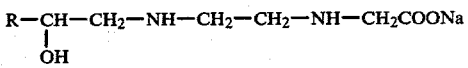

These compounds, however, readily break down where the amide link

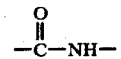

is present, or are not sufficiently hydrophillic in the presence of only one hydroxyl or ether group.

OBJECTS OF THE INVENTION

An object of the present invention is the development of amphoteric surface-active compounds which are stable over a wide pH range from acidic to alkaline over long periods of time and which have at least three hydroxyl and/or ether groups to give a greater hydrophillic effect to the molecule.

Another object of the present invention is the development of an amino-ether amphoteric surface-active compound mixture produced by reacting a glycidyl ether having the formula

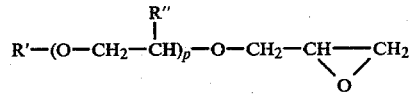

wherein R'' is a member selected from the group consisting of hydrogen and methyl; R' is a member selected from the group consisting of aliphatic primary alkyl having from 8 to 22 carbon atoms, aliphatic primary alkenyl having from 12 to 20 carbon atoms and 2-alkylalkanols having from 10 to 36 carbon atoms; and p is an integer from 0 to 3; with a substantial excess of an N-hydroxy-$C_{2-4}$-alkyl-$C_{2-6}$-alkylene diamine, removing the excess diamine, reacting the resulting substituted amino-ether with an excess of an N-alkylating agent selected from the group consisting of halo-$C_{2-4}$-alkanoic acids, halo-$C_{2-4}$-alkane sulfonic acids and halo-$C_{3-4}$-hydroxyalkane sulfonic acids, under alkaline reaction conditions and recovering said amino-ether amphoteric surface-active compound mixture.

A further object of the present invention is the development of an amino-ether amphoteric surface-active compound mixture produced by reacting a $C_{8-18}$-alkyl glycidyl ether with a substantial excess of N-hydroxyethyl-ethylene diamine, removing the excess diamine, reacting the resulting substituted amino-ether with an excess of chloroacetic acid under alkaline reacting conditions and recovering said amino-ether amphoteric surface-active compound mixture containing products of the formulae

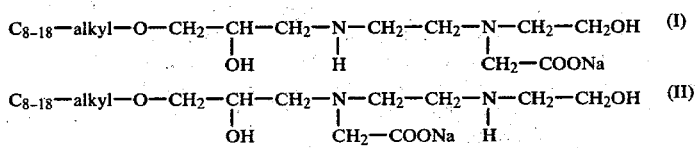

-continued $$C_{8-18}\text{-alkyl}-O-CH_2-\underset{\underset{OH}{|}}{CH}-CH_2-\underset{\underset{CH_2-COONa}{|}}{N}-CH_2-CH_2-\underset{\underset{CH_2-COONa}{|}}{N}-CH_2-CH_2OH \quad (III)$$

$$C_{8-18}\text{-alkyl}-O-CH_2-\underset{\underset{OH}{|}}{CH}-CH_2-\underset{\underset{CH_2-CH_2OH}{|}}{N}-CH_2-CH_2-\underset{\underset{H}{|}}{N}-CH_2-COONa \quad (IV)$$

$$C_{8-18}\text{-alkyl}-O-CH_2-\underset{\underset{OH}{|}}{CH}-CH_2-\underset{\underset{CH_2-CH_2OH}{|}}{N}-CH_2-CH_2-\underset{\underset{CH_2-COONa}{|}}{N}-CH_2-COONa \quad (V)$$

wherein the product of formula III represents more than 50% of said amino-ether amphoteric surface-active compound mixture.

These and other objects of the present invention will become more apparent as the description thereof proceeds.

DESCRIPTION OF THE INVENTION

The above objects have been achieved by the development of a novel amino-ether amphoteric surface-active compound mixture produced by reacting a glycidyl ether having the formula $$R'-(O-CH_2-\underset{\underset{R''}{|}}{CH})_p-O-CH_2-\underset{O}{\underset{\diagdown \diagup}{CH-CH_2}}$$

wherein R" is a member selected from the group consisting of hydrogen and methyl; R' is a member selected from the group consisting of aliphatic primary alkyl having from 8 to 22 carbon atoms, aliphatic primary alkenyl having from 12 to 20 carbon atoms and 2-alkylalkanols having from 10 to 36 carbon atoms; and p is an integer from 0 to 3; with a substantial excess of an N-hydroxy-$C_{2-4}$-alkyl-$C_{2-6}$-alkylene diamine, removing the excess diamine, reacting the resulting substituted amino-ether with an excess of an N-alkylating agent selected from the group consisting of halo-$C_{2-4}$-alkanoic acids, halo-$C_{2-4}$-alkane sulfonic acids and halo-$C_{3-4}$-hydroxyalkane sulfonic acids, under alkaline reaction conditions and recovering said amino-ether amphoteric surface-active compound mixture. The said compound mixture contains a minimum of three hydroxyl and/or ether groups and no amide linkage. It is therefore readily water-soluble and stable against hydrolysis.

The starting $C_{8-22}$-alkyl glycidyl ether has the formula A $$R'-(O-CH_2-\underset{\underset{R''}{|}}{CH})_p-O-CH_2-\underset{O}{\underset{\diagdown \diagup}{CH-CH_2}} \quad (A)$$

wherein R" is a member selected from the group consisting of hydrogen and methyl; R' is a member selected from the group consisting of aliphatic primary alkyl having from 8 to 22 carbon atoms, aliphatic primary alkenyl having from 12 to 20 carbon atoms and 2-alkylalkanols having from 10 to 36 carbon atoms; and p is an integer from 0 to 3. Preferably p is 0 and R' is alkyl having 10 to 18 carbon atoms. The glycidyl ethers are readily produced by reacting an alcohol with epichlorohydrin and subsequent dehydrohalogenation under alkaline conditions to give the epoxide. These compounds are commercially available. Among the specific alkyl glycidyl ethers which can be employed are lauryl glycidyl ether, stearyl glycidyl ether, mixed alkyl of predominately 10 and 12 carbon atoms glycidyl ether, hydrogenated coco fatty alkyl glycidyl ether, hydrogenated tallow fatty alkyl glycidyl ether, etc.

The starting N-hydroxy-$C_{2-4}$-alkyl-$C_{2-6}$-alkylene diamine has the formula B $$NH_2-(CH_2)_n-NH-(CH_2)_m-OH \quad (B)$$

where n is an integer from 2 to 6 and m is an integer from 2 to 4. These compounds are likewise commercially available. Among the specific diamines which can be employed in the reaction are, for example, N-ethanol ethylene diamine, N-propanol ethylene diamine, N-butanol ethylene diamine, N-ethanol propylene diamine, N-ethanol hexylene diamine, etc. N-ethanol ethylene diamine is preferred. This compound is also called aminoethylethanolamine (AEEA).

The first reaction of the alkyl glycidyl ether and the diamine is conducted under conditions of a substantial excess of the diamine in order to reduce the formation of di-substituted and tri-substituted diamines. The presence of large amounts of these in the alkylation reaction gives rise to turbidity in the reaction products. Preferably from 1.2 to 4 mols, especially 1.5 to 3 mols, and most particularly 2 mols, of diamine are employed per mol of glycidyl ether. The reaction is conducted at elevated temperatures and is an exothermic reaction. Ordinarily no solvents are employed but with large amounts of reactants, a low boiling solvent can be employed at the reflux to control the heat of reaction which develops. Preferably the temperature of the reaction should not exceed 175° C., and particularly should not exceed 150° C. The reaction therefore is conducted in a closed vessel which can be both heated, to initiate the reaction, and cooled, to remove the exothermic heat of reaction. After the reaction has terminated, the excess amine is removed by vacuum distillation. The reaction product is a light colored, pasty to waxy material at room temperature which gives hazy solutions in hot water.

Essentially two mono-substituted amino-ether products are produced by the reaction according to the following reaction scheme $$R-O-CH_2-\underset{O}{\underset{\diagdown \diagup}{CH-CH_2}} + \quad (C)$$

$$NH_2-(CH_2)_n-NH-(CH_2)_m-OH \longrightarrow$$

$$R-O-CH_2-\underset{\underset{OH}{|}}{CH}-CH_2-NH-(CH_2)_n-NH-(CH_2)_m-OH$$

and $$R-O-CH_2-\underset{\underset{OH}{|}}{CH}-CH_2-\underset{\underset{(CH_2)_m-OH}{|}}{N}-(CH_2)_n-NH_2 \quad (D)$$

When a sufficient excess of the diamine has been employed, the majority of the reaction product is according to formula C. It is believed that the amount of formula D in the reaction product is from about 1% to about 10% by weight.

After removal of the excess diamine, the reaction product mixture of formulae C and D is liquified by heating to a temperature between 50° C. and 98° C. An excess of the N-alkylating agent dissolved in water is added and the pH is maintained in the alkaline side by slow addition of an alkali metal hydroxide solution, while maintaining a temperature of from 70° C. to 95° C. Preferably, the pH of the reaction is maintained within range of 7 to 9, preferably 7 to 8, during the reaction.

The amount of the alkylating agent employed is at least 1.5 mols to 4 mols per mol of the substituted amino-ether products. Preferably 2 to 3.5 mols and particularly 2.5 mols of alkylating agent is employed. In order to avoid undue dilution of the reaction mixture after completion of the reaction, a limited amount of water is employed. Preferably sufficient water is employed to give a reaction product containing between 45% and 60% water.

The product obtained is a clear, slightly yellow liquor which may be used as such in formulations of liquid shampoos. It contains about 10% of NaCl, if a chloroalkylating agent was used, depending on the excess of alkylating agent and has a pH of between 8 and 9. The product obtained may be treated with an acid and behaves like a typical amphoteric compound under these circumstances and can have cationic properties at low pH ranges.

The alkylating agents which are employed are halo-$C_{2-4}$-alkanoic acids, halo-$C_{2-4}$-alkane sulfonic acids and halo-$C_{3-4}$-hydroxyalkane sulfonic acids, preferably in the form of their alkali metal salts (since the reaction is conducted under alkaline conditions). These alkylating agents have the formula E $$X-R_1-Y \quad \text{(E)}$$

wherein X is halogen, preferably chlorine, $R_1$ is a divalent radical selected from the group consisting of alkylene having 1 to 4 carbon atoms and hydroxyalkylene having 3 to 4 carbon atoms, and Y is an acid group selected from the group consisting of carboxyl and sulfonyl. The preferred alkylating agents are sodium chloroacetate, sodium chloropropionate, sodium chloroethane sulfonate and sodium 3-chloro-2-hydroxypropane sulfonate.

The reaction follows the following reaction diagram

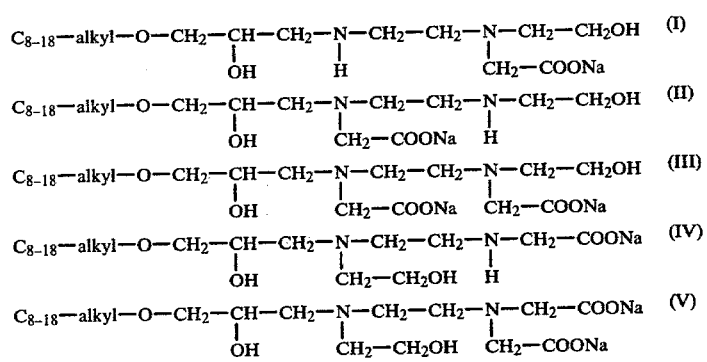

However, at least some of the reaction results in a mono-addition of the alkylating agent at either nitrogen atom and some results in a tri-addition, where the primary hydroxyl group is etherified. In addition, the small amount of the compound of formula D present also undergoes similar reactions. The final product mixture, therefore, contains the possibility of some 8 reaction products plus unalkylated compounds of formulae C and D. Most of the reaction product, however, is the di-addition product of the above formula F.

More particularly, when a $C_{8-18}$ alkyl glycidal ether is reacted with AEEA and the product alkylated with sodium chloroacetate, the resulting product is an amino-ether amphoteric surface-active compound mixture containing products of the formulae

wherein the product of formula III represents more than 50% of said amino-ether amphoteric surface-active compound mixture, The following examples are illustrative of the practice of the invention without being limitative in any respect.

EXAMPLE 1

Step A 572 gm (about 2 mols) of a $C_{12-14}$-alkyl glycidyl ether and 416 gm (about 4 mols) of aminoethyl ethanolamine (AEEA) were charged in a 2000 ml glass reaction flask equipped with a stirrer and condenser. Nitrogen gas was sparged through the flask. The reaction mixture was heated to 70° C. with stirring over a period of 30 minutes. At this temperature, an exothermic reaction commenced and the temperature rapidly increased to 140° C. The temperature was maintained at 140° C. for 10 minutes by means of a water cooling bath. Thereafter, the temperature was brought to 150° C. by heating and maintained at this temperature for 1 hour.

The AEEA was then removed by vacuum distillation at temperatures of from 150° C. to 170° C. and an increasing vacuum of from 15 to 2 Torr. A yield of distillate of 239 gm was obtained which was a pale green liquid analyzing 86.5% AEEA and 2.1% $H_2O$. 727 gm of reaction product remained. When cooled below 60° C., the product was a light yellow paste. According to the amount of distillate recovered, the reaction product consisted almost entirely of the adduct of 1 mol of ether and 1 mol of AEEA. The reaction product was soluble in water at 90° C. to give a hazy solution. The epoxide oxygen content was well below 1%.

Step B 390 gm (about 1 mol) of the reaction product of Step A was charged into a stirrer equipped 20 liter roundbottom glass flask supplied with a dropping funnel and a condenser. The reaction product was heated to 70° C. until it became liquid. 298 gm (about 2.5 mols) of sodium chloroacetate was dissolved in 688 gm of water. The amount of water is sufficient to give a 50% solution of the reactants. This solution was added to the melted reaction product and the temperature was brought to 80° C. A pH electrode was immersed in the reaction mixture and a pH of approximately 8 was observed. The pH was maintained at approximately 7 to 8 through the dropwise addition of a 50% solution of NaOH. 152 gms (about 2 mols) was added over 100 minutes while the temperature of the reaction mixture slowly increased to 95° C.

The temperature was maintained at 95° C. with stirring for another 100 minutes. The pH did not change, indicating completion of the reaction. A yield of 1481 gms of amphoteric surface-active compound mixture, in solution, was obtained as a clear, pale amber liquid having a content of 9.6% NaCl (about 100% of theory) and 52.6% of $H_2O$. The pH of a 10% solution at room temperature was 8.6. No change in properties of the product were apparent after storage for two years.

Evaluation

The amphoteric surface-active compound produced in solution above had the probable formulae

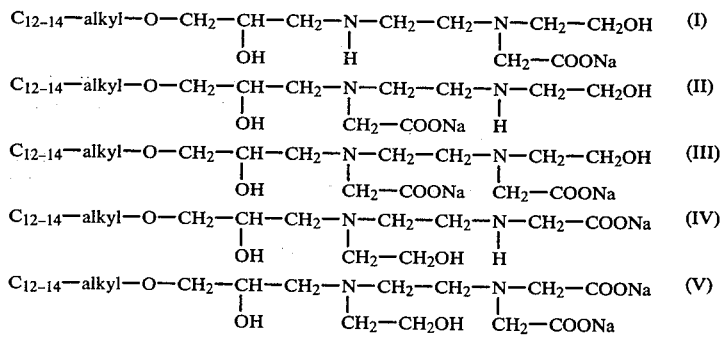

wherein the product of formula III represents more than 50% of said amino-ether amphoteric surface-active compound mixture.

The compound mixture gives clear, stable solutions in water, 20% $H_2SO_4$, 20% NaOH and typical shampoo compositions in combination with fatty alcohol ether sulfates.

The product was evaluated for physical properties, performance in standard formulations and ocular irritation tests. These results were compared with the results obtained with a standard amphoteric "Standapol CIM-40" which has the probable formula

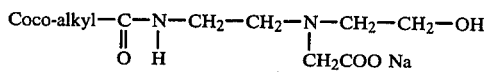

and is present in solution as a 40% solids content (9% NaCl).

A. Physical Properties
1. Analytical Data:

| | |
|---|---|
| % Water: | 52.6% |
| % Chloride: | 9.6% |
| pH (10% solution): | 8.6 |
| Viscosity: | 3,800 cps (Brookfield, 10 rpm, Spindle No. 3, 25° C.) |

2. Stability in Acids, Bases and Salts:

| | |
|---|---|
| Acid stability $H_2SO_4$ (20% solution) | No separation, haze or sediment at 10%. |
| Base stability NaOH (20% solution) | No separation, haze or sediment at 10%. |
| Salt stability NaCl (20% solution) | No separation, haze or sediment at 10%. |

B. Comparisons
1. Foaming Properties (Ross-Miles Test, Modified)
   (a) Test conditions:

| Product | Foam height, in ml |
|---|---|
| Example 1 | 250/235 |
| Standapol CIM-40 | 255/240 |

(b) Test conditions:

| Product | Foam Height, in ml |
|---|---|
| Example 1 | 350/325 |
| Standapol CIM-40 | 350/325 |

C. Shampoo Formulations: The product of Example 1 was evaluated for viscosity, foaming properties, and cloud point determinations.

| Shampoo No. 1 | A | B |
|---|---|---|
| Water | 57.5 | 57.5 |
| Propylene Glycol | 1.0 | 1.0 |
| Standamid SD | 0.5 | 0.5 |
| Standapol WAQ Spec. | 16.0 | 16.0 |
| Standapol CIM-40 | 25.0 | — |
| Example 1 | — | 25.0 |
| pH (adjusted to): | 7.0 | 7.0 |

-continued

| Shampoo No. 1 | A | B |
|---|---|---|
| Viscosity: | 880 cps | 20,000 cps |
| Foam Performance: | 180/165 | 185/175 |
| Cloud Point: | Below 0° C. | Below 0° C. |

| Shampoo No. 2 | A | B |
|---|---|---|
| Water | 62.50 | 62.50 |
| Sodium Chloride | 1.00 | 1.00 |
| Standapol ES-2 | 10.00 | 10.00 |
| Standapol 130-E | 12.00 | 12.00 |
| Standapol CIM-40 | 12.00 | — |
| Example 1 | — | 12.00 |
| pH (adjusted to): | 7.0 | 7.0 |
| Viscosity: | 200 cps | 350 cps |
| Cloud Point: | Below 0° C. | Below 0° C. |
| Foam Performance: | 165/160 | 170/155 |

From the data listed above it appears that in the second shampoo formulation, both products behave fairly evenly. In the first shampoo formulation, the viscosity differences are quite noticeable; this is not considered a deterrent.

D. Irritation Studies

| Product | Recording |
|---|---|
| Standapol CIM-40 (full strength) | Produced a conjunctival irritation which cleared on the seventh day. |
| Example 1 (full strength) | Produced a conjunctival irritation which cleared on the seventh day. |
| Standapol CIM-40 25% active | Produced a conjunctival irritation which cleared on the seventh day. |
| Example 1 25% active | Produced a conjunctival irritation which cleared on the third day. |

The product of Example 1 was satisfactory in ocular irritation studies and performed better than the standard amphoteric employed in shampoos.

E. Hydrolysis Studies

Samples of Standapol CIM-40 and the product of Example 1 were each refluxed in 20% sodium hydroxide and 20% sulfuric acid for 7 hours. At the end of the experiment the CIM-40 solutions were visibly altered while the solutions of the product of Example 1 were unchanged. A solid was floating on the acidic hydrolysis of the CIM-40 while the alkaline hydrolysis was filled with a gelatinous solid.

The alkaline hydrolysis was acidified to a pH 3, filtered and diluted to approximately a 1% concentration (initial concentration=5%) and the surface tension determined by the stalagmometer method. The same procedure was followed for the product of Example 1, but, of course, there was no initial solid.

For the acidic hydrolyses, the solutions were diluted to a 1% "active" concentration and the surface tension was then measured; again, the CIM-40 had a solid while the compound of the invention did not.

The results are summarized as follows:

Surface Tensions of Hydrolyses of Amphoteric Agents

| Substance | Solution | Surface Tension (dyne/cm) Before | After |
|---|---|---|---|
| CIM-40 | 20% NaOH | 55.9 | 64.6 |
| CIM-40 | 20% $H_2SO_4$ | 19.9 | 54.4 |
| Example 1 | 20% NaOH | 66.4 | 65.5 |
| Example 1 | 20% $H_2SO_4$ | 34.2 | 32.1 |

The surface tensions indicate that there has been substantial degradation of the CIM-40 in both solutions; the visible evidence of, apparently, fatty acid and soap also tends to confirm this conclusion. Both of these phenomena are absent in the case of the product of Example 1.

EXAMPLE 2

About 1 mol of the reaction product of Example 1, Step A, was charged into a stirrer equipped glass flash supplied with a dropping funnel and a condenser. After heating to 70° C. to liquefy it, about 2.5 mols of sodium 2-hydroxy-3-chloro-propane sulfonate dissolved in sufficient water to give an about 50% solution was added thereto at 70° C. The sodium 2-hydroxy-3-chloro-propane sulfonate is produced by the reaction of epichlorohydrin with sodium bisulfite. The temperature of the solution was maintained at 70°-90° C. while adding about 2 mols of a 50% aqueous solution of sodium hydroxide. After cooling, an amphoteric surface-active compound mixture of about 40% active solution was obtained. The active compound had the probable formulae

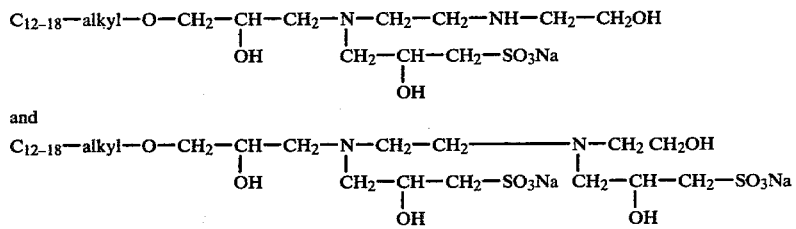

and with the latter predominating. The product has comparable stability values and surface-active properties to those of the product of Example 1.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. An amino-ether amphoteric surface-active compound mixture produced by reacting a glycidyl ether having the formula

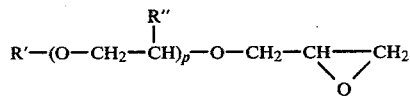

wherein R" is a member selected from the group consisting of hydrogen and methyl; R' is a member selected from the group consisting of aliphatic primary alkyl having from 8 to 22 carbon atoms, aliphatic primary alkenyl having from 12 to 20 carbon atoms and 2-alkylalkanols having from 10 to 36 carbon atoms; and p is an integer from 0 to 3; with a substantial excess of an N-hydroxy-$C_{2-4}$-alkyl-$C_{2-6}$-alkylene diamine, removing the excess diamine, reacting the resulting substituted amino-ether with from 1.5 mols to 4 mols per mol of said substituted amino-ether of an N-alkylating agent selected from the group consisting of halo-$C_{2-4}$-alkanoic acids, halo-$C_{2-4}$-alkane sulfonic acids and halo-$C_{3-4}$-hydroxyalkane sulfonic acids, under alkaline reaction conditions maintained by the addition of an alkali metal hydroxide solution, and recovering said amino-ether amphoteric surface-active compound mixture.

2. An aqueous solution containing from 0.05% to 50% by weight of the amino-ether amphoteric surface-active compound mixture of claim 1.

3. An amino-ether amphoteric surface-active compound mixture produced by reacting a $C_{8-18}$-alkyl glycidyl ether with a substantial excess of N-hydroxyethyl-ethylene diamine, removing the excess diamine, reacting the resulting substituted amino-ether with an excess of chloroacetic acid under alkaline reacting conditions in the presence of sodium hydroxide solution and recovering said amino-ether amphoteric surface-active compound mixture containing products of the formulae

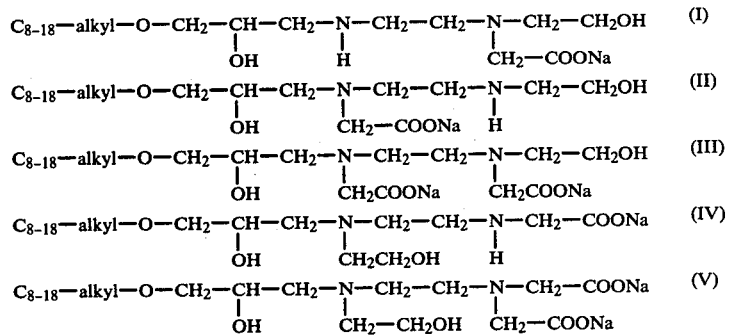

wherein the product of formula III represents more than 50% of said amino-ether amphoteric surface-active compound mixture.

4. An aqueous solution containing from 0.05% to 50% by weight of the amino-ether amphoteric surface-active compound mixture of claim 3.

UNITED STATES PATENT AND TRADEMARK OFFICE
CERTIFICATE OF CORRECTION

PATENT NO. : 4,214,102
DATED : July 22, 1980
INVENTOR(S) : PETER LEENDERS

It is certified that error appears in the above—identified patent and that said Letters Patent is hereby corrected as shown below:

Column 6, line 7: "$_4$NaOH" should read -- 4 NaOH --.

Column 8, line 29: Below "(a) Test conditions:" insert -- 100 ml of 0.1% active, 25°C, Tap Water --.

line 36: Below (b) Test conditions:" insert -- 100 ml of 0.1% active, 40°C, Tap Water --.

Signed and Sealed this

Seventh Day of July 1981

[SEAL]

Attest:

RENE D. TEGTMEYER

*Attesting Officer*   *Acting Commissioner of Patents and Trademarks*